United States Patent [19]

O'Leary et al.

[11] Patent Number: 4,911,702
[45] Date of Patent: Mar. 27, 1990

[54] ATTACHMENT MEANS AND INCONTINENT GARMENT INCORPORATING SAME

[75] Inventors: Audrey A. O'Leary, Belfair; Raimo K. Rahkonen, Gig Harbor, both of Wash.

[73] Assignee: Weyerhaeuser Company, Tacoma, Wash.

[21] Appl. No.: 230,109

[22] Filed: Aug. 9, 1988

[51] Int. Cl.⁴ .............................. A61F 13/16
[52] U.S. Cl. .................... 604/389; 604/385.2
[58] Field of Search ............ 604/389, 390, 385.1

[56] References Cited

U.S. PATENT DOCUMENTS

| | | | |
|---|---|---|---|
| 3,800,796 | 4/1974 | Jacob | 128/284 |
| 4,050,121 | 9/1977 | Richman | |
| 4,074,716 | 2/1978 | Schaar | 128/287 |
| 4,090,516 | 5/1978 | Schaar | 128/287 |
| 4,136,698 | 1/1979 | Mesek | 128/287 |
| 4,209,016 | 6/1980 | Schaar | 604/390 |
| 4,210,144 | 7/1980 | Sarge | 128/287 |
| 4,237,890 | 12/1980 | Laplanche | 128/287 |
| 4,369,786 | 1/1983 | Miller | 604/390 |
| 4,389,212 | 6/1983 | Tritsch | 604/389 |
| 4,609,373 | 9/1986 | Johnson | 604/390 |
| 4,670,012 | 6/1987 | Johnson | 604/390 |
| 4,681,581 | 7/1987 | Coates | 604/391 |
| 4,826,499 | 5/1989 | Ahr | 604/389 |

*Primary Examiner*—Stephen C. Pellegrino

[57] ABSTRACT

The invention is an attachment means for an incontinent garment or diaper. It is particularly useful with a garment which has a relatively long, as measured in a longitudinal direction, waist or abdominal encircling portion. Prior known garments of this type normally require two adhesive attachment tabs. One of these is used to tighten the leg encircling portion of the garment and the other the waist encircling portion. The present invention accomplishes this with a single adhesive tab. The attachment system has an elastic anchor strip adjacent the longitudinal margins of the rear waist encircling portion of the garment. This is attached at each end with an unattached free zone in the center. A single attachment tab has one end located on the anchor strip and is generally normal thereto. When the garment is put in place on a wearer, the anchor strip serves as a yoke to simultaneously place tension around the waist area and leg areas of the garment.

4 Claims, 2 Drawing Sheets

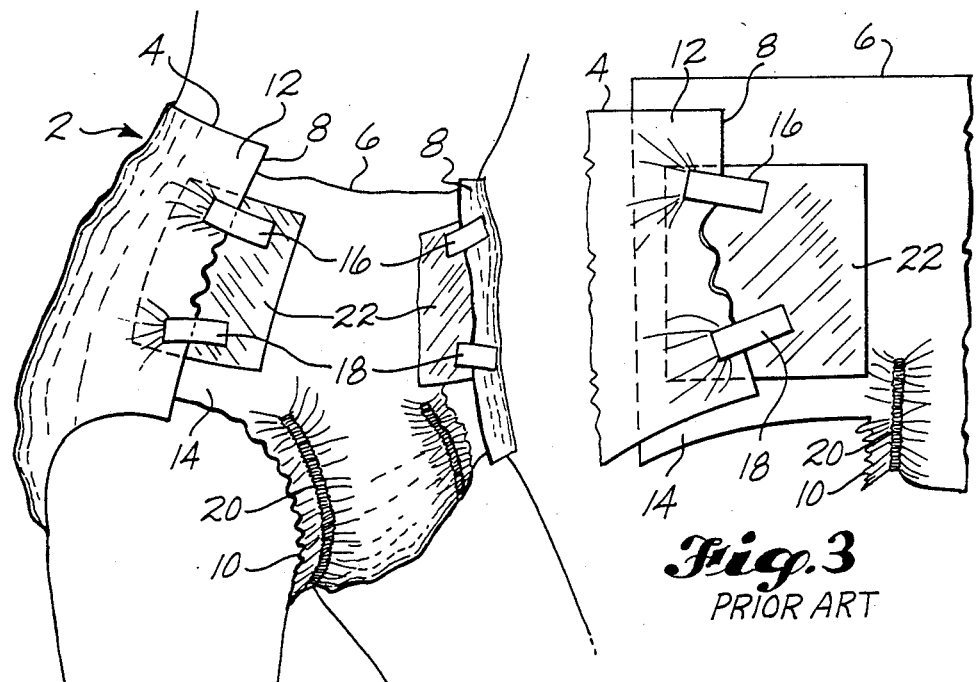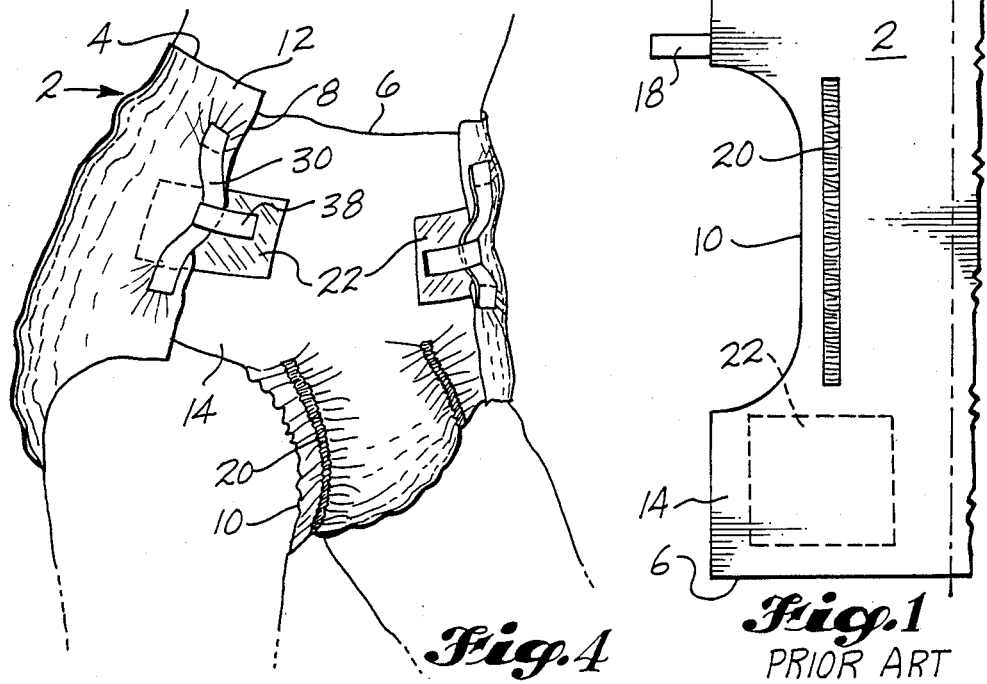

ATTACHMENT MEANS AND INCONTINENT GARMENT INCORPORATING SAME

BACKGROUND OF THE INVENTION

The present invention is an attachment means for an incontinent garment or diaper by which it can be readily and conveniently secured about a wearer. In particular, the attachment means uses a convenient single adhesive tab which directs tension around both the leg and waist areas to prevent leakage.

Adhesive attachment tabs for disposable diapers have been in use for almost two decades. They normally consist of a pair of pressure sensitive adhesive tabs, one on either side of the rear panel of the diaper. These are secured to the waist encircling portion to securely hold the diaper when it is in place on a wearer. Many improvements have been made in adhesive attachment tabs since they were first introduced.

More recently, disposable diapers or similar garments for incontinent adults have become available. Because of major differences in anatomy and body proportions, these are not simply scaled up version of disposable diapers intended for infants. The normal angle of the legs with regard to the torso is quite different in an adult than in a baby. In addition, a significantly longer abdominal portion is required in an adult garment. Various forms of elastic attachment means are also commonly used. These range from single straps, such as are shown in U.S. Pat. No. 4,670,012 to Johnson, to double straps, such as are shown in European Patent Application 0,120,790. However, the incontinent garments shown in these two patents are not typical of those which presently have the most widespread acceptance. The most popular incontinent garments today have wing-like waist and abdominal encircling portions at each end. These are usually about 160–200 mm in the longitudinal dimension so that they completely cover the buttocks and abdomen of the wearer. In an incontinent garment of this type two pairs adhesive attachment tabs have been desirable. One pair is located on opposite sides at the extreme end of the rear panel of the garment and serves to provide tight securement about the waist of the wearer. The other pair is at the bottom of the wing-like portion, where it serves to provide leak resistant securement about the leg of the wearer. Thus, in a garment of this type there are four adhesive tabs to properly adjust as opposed to only two in a baby diaper.

Very often when an incontinent garment is placed on an adult, it is necessary to readjust the original placement of the tapes in order to achieve a tight and comfortable fit. This last task has been made simpler by the use of a target tape area on the abdominal portion of the diaper. The attachment tapes may be peeled from this target tape area without tearing the moisture impermeable backing film and then repositioned. However, it would be desirable from a number of standpoints if a single attachment tape could be made to serve the function of the two tapes presently used. This feature of convenience has been repeatedly requested by nurse's aides who must place the incontinent garment on bedridden patients.

Elasticized attachment tapes have been proposed in order to assure better fit when placing a diaper or incontinent garment on a person, although these have not yet found widespread usage. Examples are found in the following three closely-related U.S. patents to Schaar: Nos. 4,074,716; 4,090,516; and 4,209,016. These patents show elasticized fasteners in various configurations which include double tapes or tapes with split Y-shaped end portions. Other elastic fastener tapes are found in U.S. Pat. Nos. 3,800,796 to Jacob; 4,237,890 to Laplanche; 4,389,212 to Tritsch; and in European Patent Application 0,191,355; and in West German Applications 3,419,621 and 3,419,623. These patents to which reference has just been made are illustrative only and the list is not considered to be fully inclusive.

The present invention has overcome many of the problems associated with the use of double attachment tapes and, in particular, those problems which were present with their use on adult incontinent products.

SUMMARY OF THE INVENTION

The present invention is an attachment means for an incontinent garment or diaper. The invention is further directed to an incontinent garment or diaper having an attachment means of the type to be described.

In the description which follows, the term incontinent garment will be used for simplicity but it should be understood that that term refers equally to garments which are suitable for wear by infants or adults.

In general the incontinent garments will have a moisture absorbing pad, usually made of cellulose fluff, enclosed within a moisture permeable nonwoven, body contacting cover sheet and a generally coextensive moisture impermeable backing sheet. The latter is typically made of a pigmented polyethylene film about 0.025 mm (0.001 inch) in thickness. The garment will have waist encircling portions at each end. These waist encircling portions have both transverse and longitudinal margins, the latter lying along longitudinal edges of the garment. Each longitudinal edge of the garment will have a generally centrally located leg encircling portion which adjoins the longitudinal margins of the waist encircling portions. The attachment means of the present invention comprises an elongated anchor strip which is adjacent and generally parallel to the longitudinal margins of one of the waist encircling portions, normally the one along the back of the wearer. The ends of each anchor strip are permanently attached to the body of the garment leaving an unattached free zone between each end. One of the attached ends is located adjacent the transverse margin of the waist encircling portion and the other is located adjacent the leg encircling portion of the longitudinal edge. An outwardly oriented attachment tape has a proximal end located on and generally normal to the anchor strip. The distal end of the attachment tape has a pressure sensitive adhesive on one face. This is normally covered or attached to a release surface until such time as it is desired to place the garment on a wearer. At that time the attachment tape is peeled off of the release paper and the adhesive surface is used to secure the garment.

In the most preferred form of the invention, the anchor strip is an elastic ribbon which can be significantly stretched when the incontinent garment is in use. By this means the anchor strip simultaneously places tension around the waist and leg areas while only using a single attachment tape.

In one version of the invention the attachment tape is in fixed position on the anchor strip. In another embodiment, the attachment tape is free to slide along the anchor strip to allow greater versatility in placement.

It is an object of the invention to provide an improved adhesive attachment device for an adult incontinent garment or infant diaper.

It is another object to provide an attachment means for an incontinent garment whereby a single adhesive tape simultaneously places tension around the waist and leg areas of the garment.

It is a further object to provide an incontinent garment that can be more readily and conveniently applied to a wearer.

It is yet another object to provide an incontinent garment having an attachment device that is self-adjusting for different body positions.

These and many other objects will become readily apparent to those skilled in the art upon reading the following detailed description taken in conjunctions with the drawings.

BRIEF DESCRIPTION OF THE DRAWINGS

FIG. 1 is a plan view of a prior art incontinent pad, partially cut away.

FIG. 2 is a representation of the incontinent pad of FIG. 1 on a user.

FIG. 3 shows detail of the attachment zone of the incontinent pad of FIG. 1.

FIG. 4 shows an incontinent pad using the attachment system of the present invention in place on a user.

DESCRIPTION OF THE PREFERRED EMBODIMENTS

Figure 5:
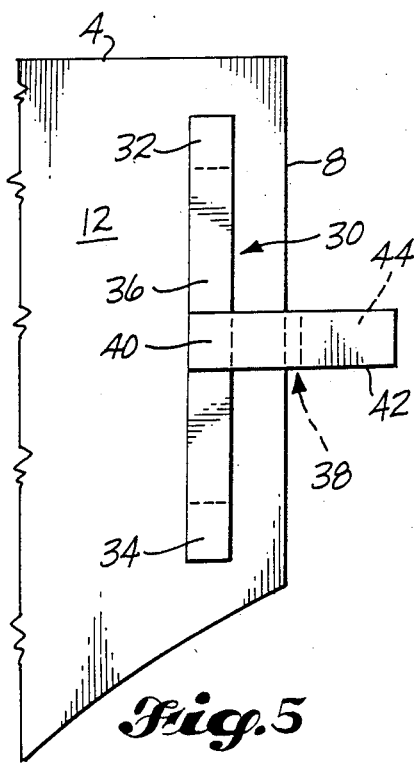
FIGS. 5 and 6 show details of one embodiment of the attachment system of the present invention.

Referring now to the figures, an incontinent pad 2 is seen to have a rear lateral or waist margin 4 and a front lateral or waist margin 6. The pad also has longitudinal margins 8 which are interrupted by leg cutout zones 10. The pad is thus seen to have an overall somewhat hour-glass-type configuration. As such, it has rear generally trapezoidal wing-shaped portions 12 and front generally trapezoidal wing-shaped portions 14. The rear wing-shaped portions 12 has an adhesive waist attachment tab 16 and leg zone attachment tab 18. Parallel to the leg cutout zone is a longitudinal elastic insert 20. A target tape 22 may optionally be used on the outside surface of the diaper which covers the abdominal zone. This serves as an attachment point for both of the attachment tabs 16 and 18 so that, if desired, they may be repositioned without tearing the thin polyethylene backing film.

FIG. 2 shows the above incontinent pad as it would appear when in place on a wearer.

FIG. 3 is a detailed representation of the attachment zone of the incontinent pad shown in FIGS. 1 and 2. Note that the adhesive tab 16 serves to keep the diaper tight around the waist area of the wearer while tab 18 serves the same function around the leg zone. A snug fit at both of these locations is essential to reduce leakage. It is usually desirable to allow the longitudinal edge portion between the attachment tapes to pucker somewhat for ventilation.

FIG. 4 shows an incontinent pad using the attachment tape of the present invention as it would appear during use. Here the original attachment tapes 16 and 18 have been replaced by an assembly which consists of an anchor strip 30 having fixed to it a single attachment tab 38. Note that the optional target zone 22 can be considerably reduced in size.

One particular advantage of an incontinent pad using the attachment device of the present invention is its high degree of self-adjustability for differing body positions. For example, a garment of the two-tape type, as shown in FIGS. 1–3, might fit well when placed on a person in a reclining position but fit poorly in a standing position. This problem is largely overcome using the present attachment device.

Figure 6:
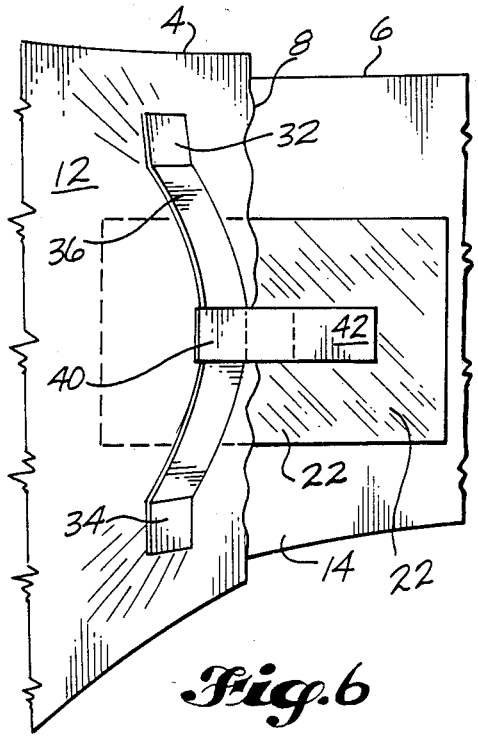

Reference should now be made to FIGS. 5 and 6. Anchor strip 30 is preferably made of an elastic material. This can be natural rubber or an equivalent synthetic material, preferably one having an extensibility of at least about 100%. The ends 32, 34 of anchor strip 30 are permanently bonded to the body of the incontinent pad, preferably to a reinforced area of the backing sheet. This leaves a free or unattached zone 36 between the bonded ends. End 32 is joined to the body near the rear lateral margin 4 close to its junction with the longitudinal margin 8. The other end 34 of the anchor strip is bonded to the body of the diaper near the junction of wing portion 12 with the leg cutout zone 18. Thus, anchor strip 30 is seen to lie adjacent to and generally parallel to the longitudinal margin 8 of the waist encircling portions of the diaper.

The attachment tab 38 is fixed at its proximal end 40 to free zone 36 of anchor strip 30. The distal end 42 of the attachment tab has on one surface a pressure sensitive adhesive 44. This adhesive serves to bond the tab to the abdominal surface of the incontinent pad when in use.

Figure 7:
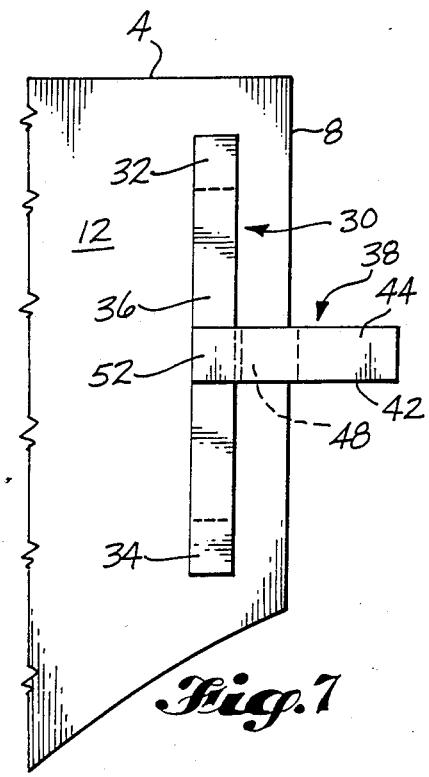
FIGS. 7 and 8 show details of an alternative embodiment of the present invention.
Figure 8:
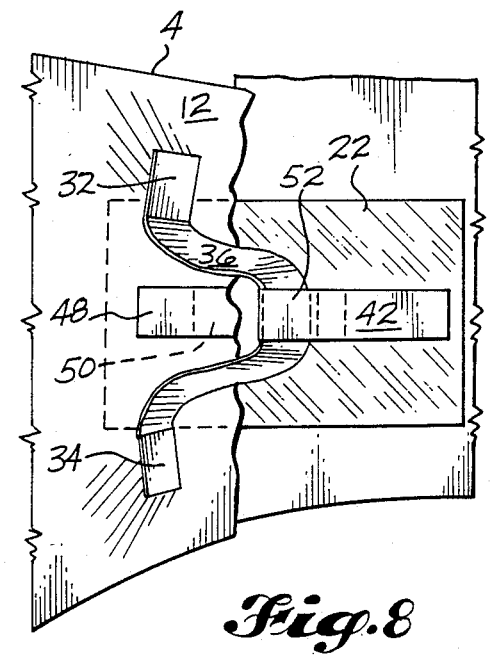

FIGS. 7 and 8 show an alternative version of the attachment system. Here the attachment tab 38 has a proximal end 52 which is slidably joined to anchor strip 36. This enables more versatility in positioning adhesive tab 42 in order to secure a tight and comfortable fit.

As seen in FIGS. 7 and 8 there is a release strip 48 permanently affixed to wing portion 12. This has one end 50 wrapped around the garment. The adhesive surface 44 of tab 38 is normally held against this release paper prior to use of the garment. Other relationships of attachment tabs and release strips will be apparent to those skilled in the art.

EXAMPLE

A standard medium size adult incontinent pad was made as follows: the cover sheet was thermally bonded polypropylene nonwoven material, Type APN-251, supplied by James River Corp., Simpsonville, S.C. The backing sheet was 0.033 mm (0.0013 in) microtextured polyethylene, available from Clopay Corporation, Cincinnati, Ohio. A tissue overwrapped bleached kraft fluff pad was sandwiched between the cover and backing sheet and bonded to the latter using fine line hot melt adhesive strips placed on 19 mm centers. The fluff pad weighed about 93 grams and was generally rectangular, although constricted somewhat in the central portion. The incontinent garment had overall dimensions of 635 mm in width and 812 mm in length with a constricted central leg encircling portion 250 mm in width. The absorbent pad had dimensions of about 660 mm in length and 220 mm in width with the central portion being about 160 mm wide. There was a pad-free area about 90 mm long at the rear waist encircling area and about 70 mm long at the front waist encircling area. The trapezoidal wings 12 and 14 (see FIG. 1) at each end of the product were also pad-free. The transverse width of each wing portion at the rear waist encircling area, as measured from the projection of leg cutout line 10, was about 193 mm with a length of the outside longitudinal margin 8 of 212 mm. The length of the inside margin of the trapezoidal portion, measured along the projection of leg cutout line 10 from the rear marginal edge 4 to the leg cutout portion was approximately 340 mm.

An anchor tape 30 was inset about 15 mm from each longitudinal edge 8 of the rear wing portions. This was made of a urethane elastic material having a width of 7.2 mm and a thickness of 0.071 mm (0.29 in×0.0028 in) The overall length of the anchor tape was 140 mm and the unattached free zone between the ends was 107 mm. The ends were bonded directly to the polyethylene backing film. A pressure sensitive adhesive tab 35 mm in width to the central portion of the anchor tape. The attachment tabs had free ends extending approximately 25 mm beyond the edge of the incontinent pad. This arrangement enabled the garment to be readily and comfortably put in place on a wearer with a minimum of adjustment being necessary.

Having thus described the best mode known to the inventor of practicing her invention, it will be apparent to those skilled in the art that many variations would be possible without departing from the spirit of the invention. Thus, the invention is to be considered as limited only by the following claims.

We claim:

1. An attachment means for an incontinent garment or diaper of the type comprising a moisture absorbing pad enclosed within a moisture permeable body contacting cover sheet and a generally coexistive moisture impermeable backing sheet, each end of this garment having a waist encircling portion with transverse and longitudinal margins, the longitudinal margins lying along longitudinal edges of the garment, said longitudinal edges further having leg encircling portions, which comprises:

elongated anchor strip means adjacent and generally parallel to the longitudinal margins of one waist encircling portion, the ends of said anchor strip means being permanently attached to the body of the garment with an unattached free zone therebetween, one of said attached ends being located adjacent the transverse margin of the waist encircling portion and the other located adjacent the leg encircling portion of the longitudinal edge;

an outwardly oriented attachment tape means generally normal to the anchor strip means, the attachment tapes means having a proximal end slidably located on the free zone of anchor strip means and a distal end, the distal end having a pressure sensitive adhesive on one face thereof for holding the garment in place while in use, whereby when the garment is in place on a wearer the anchor strip means serves as a yoke to simultaneously place tension around the waist area and leg areas using the single attachment tape means.

2. The attachment means of claim 1 in which the anchor strip means is an elastic material.

3. An incontinent garment or diaper of the type comprising a moisture absorbing pad enclosed with a moisture permeable body contacting cover sheet and a generally coextensive moisture impermeable backing sheet, which comprises:

wing-like waist encircling portions located at each end, with a constricted crotch zone therebetween so as to create a generally hourglass-shaped outline, said waist encircling portions having transverse and longitudinal margins;

anchor strip means adjacent and generally parallel to the longitudinal margins of the waist encircling portion at one end of the garment, said anchor strip means being permanently attached at each end to the body of the garment with an unattached free zone in the middle section;

an outwardly oriented attachment tape means generally normal to the anchor strip means, the attachment tape means having a proximal end slidably located on the free zone of anchor strip means and a distal end, the distal end having a pressure sensitive adhesive on one face thereof for holding the garment in place while in use, whereby when the garment is in place on a wearer the anchor strip means serves as a yoke to simultaneously place tension around the waist area and leg areas using the single attachment tape means.

4. The incontinent garment or diaper of claim 3 in which the anchor strip means is an elastic material.

* * * * *